United States Patent
Sigg et al.

(10) Patent No.: US 6,555,719 B2
(45) Date of Patent: Apr. 29, 2003

(54) PROCESS FOR THE THERMAL AFTER-TREATMENT OF CLEAVAGE PRODUCT FROM THE ACID-CATALYZED CLEAVAGE OF CUMENE HYDROPEROXIDE

(75) Inventors: Reinhard Sigg, Marl (DE); Uwe Tanger, Bochum (DE); Manfred Weber, Haltern (DE); Otto Schnurr, Kapellen (BE); Hugo H.J.M. Liefooghe, Edegem (BE)

(73) Assignee: Phenolchemie GmbH & Co. KG, Gladbeck (DE)

( * ) Notice: Subject to any disclaimer, the term of this patent is extended or adjusted under 35 U.S.C. 154(b) by 0 days.

(21) Appl. No.: 09/847,393

(22) Filed: May 3, 2001

(65) Prior Publication Data

US 2001/0039362 A1 Nov. 8, 2001

(30) Foreign Application Priority Data

May 3, 2000 (DE) ........................................ 100 21 482

(51) Int. Cl.⁷ .............................................. C07C 37/08
(52) U.S. Cl. ...................................... 568/798; 568/716
(58) Field of Search ................................ 568/716, 715, 568/798

(56) References Cited

U.S. PATENT DOCUMENTS

| 4,358,618 A | * | 11/1982 | Sifniades et al. | ............ 568/385 |
| 5,245,090 A | * | 9/1993 | DeCaria et al. | ............. 568/798 |
| 5,530,166 A | * | 6/1996 | Zakoshansky | .............. 568/598 |
| 6,057,483 A | * | 5/2000 | Zakoshansky | .............. 568/798 |
| 6,307,112 B1 | * | 10/2001 | Weber et al. | ................ 568/798 |

FOREIGN PATENT DOCUMENTS

DE     197 55 026     6/1998

* cited by examiner

*Primary Examiner*—Jean F. Vollano
(74) *Attorney, Agent, or Firm*—Oblon, Spivak, McClelland, Maier & Neustadt, P.C.

(57) ABSTRACT

The cleavage product from the acid-catalyzed cleavage of cumene hydroperoxide into phenol and acetone is subjected to thermal after-treatment by a process, which comprises heating the cleavage product in a reactor, wherein the heat supplied for the thermal treatment is the heat generated by at least one exothermic reaction which occurs in the reactor. The exothermic reaction which proceeds in the cleavage product is preferably the cleavage of cumene hydroperoxide.

12 Claims, 2 Drawing Sheets

PROCESS FOR THE THERMAL AFTER-TREATMENT OF CLEAVAGE PRODUCT FROM THE ACID-CATALYZED CLEAVAGE OF CUMENE HYDROPEROXIDE

BACKGROUND OF THE INVENTION

1. Field of the Invention

The present invention relates to an improved process for selective, energy-saving thermal after-treatment of cleavage product from the acid-catalyzed cleavage of cumene hydroperoxide (CHP) into phenol and acetone.

2. Description of the Background

The process of acid-catalyzed cleavage of cumene hydroperoxide into phenol and acetone has long been of particular industrial importance. In the preparation of phenol from cumene by the Hock process, cumene is oxidized to cumene hydroperoxide (CHP) in a first reaction step, known as oxidation, and the CHP is subsequently concentrated to 65 to 90% by weight in a vacuum distillation, known as concentration. In a second reaction step, known as cleavage, the CHP is cleaved into phenol and acetone in the presence of an acid, usually sulfuric acid. Here, the dimethyl phenyl carbinol (DMPC) formed in the oxidation is partly dissociated into α-methylstyrene (AMS) and water in an equilibrium reaction, and a further part of the DMPC reacts with CHP to form dicumyl peroxide (DCP), while the remainder of the DMPC remains in the cleavage product. After neutralization of the cleavage product, this product mixture is worked-up by distillation.

During the cleavage, part of the AMS forms high boiling compounds, i.e. high boilers such as dimers and cumylphenols, which are discharged as a residue from the distillation apparatus. The AMS still present after the neutralization is hydrogenated to cumene during the distillation and is recirculated to the oxidation step. DMPC which has not reacted in the cleavage reaction passes as a high boiler to the residue, and part of it reacts further in the hot phenol columns to form AMS from which high-boiling secondary components are in turn formed. The DCP is stable at customary cleavage temperatures (50 to 70° C.). In the hot phenol columns, it decomposes thermally to form, in the inventor's experience, primarily o-cresol. On the other hand, in the presence of acid, DCP can be cleaved into phenol, acetone and AMS at temperatures to above 80° C. It is, therefore, obvious to react the residual DMPC and the DCP formed in the cleavage completely immediately after the cleavage by means of a targeted increase in the temperature in the presence of the acid used as catalyst in the cleavage.

In this way, DMPC is converted virtually completely into AMS, and DCP is converted completely into phenol, acetone and likewise AMS.

Such a thermal after-treatment of the cleavage product has already been described in U.S. Pat. No. 2,757,209, where temperatures above 100° C., especially from 110 to 120° C., were used. The objective of this thermal after-treatment is complete dehydration of the DMPC to AMS. In contrast, U.S. Pat. No. 4,358,618 describes a thermal after-treatment which has as its objective the complete conversion of the DCP formed in the cleavage into phenol, acetone and AMS, using temperatures ranging from 120 to 150° C. U.S. Pat. No. 5,254,751 describes a thermal after-treatment with the same objective as U.S. Pat. No. 4,358,618, using temperatures ranging from 80 to 110° C. Finally, in DE 197 55 026 A1, the after-treatment is conducted in a temperature range above 150° C. Accordingly, the optimum temperature ranges specified for the thermal after-treatment of cleavage product from phenol production differ widely in the disclosures hitherto.

In all these previously described processes, the cleavage product is first heated by means of steam in heat exchangers in order to conduct the thermal after-treatment and, after a sufficient reaction time, the product is cooled again by means of water in heat exchangers. Depending on the temperature selected for the thermal after-treatment, this gives specific steam consumptions of 0.2 metric tons of steam per metric ton of phenol. We have found that increased deposition of high-boiling by-products in the heat exchangers (fouling) of the thermal after-treatment generally occurs at temperatures above 100° C., especially above 120° C., and this fouling is associated with a drastic decrease in heat transfer. Particularly in the apparatuses for heating the product by means of steam, organic deposits form on the hot heat exchange surfaces on the product side, so that these apparatuses have to be cleaned at relatively short intervals of a few weeks. This fouling increases further as the temperatures increases. A need, therefore, exists for a process modification which reduces fouling.

SUMMARY OF THE INVENTION

Accordingly, one object of the invention is to provide a process for the thermal after-treatment of cleavage product from cumene hydroperoxide cleavage, which displays not only high selectivity but also low energy costs and a high availability because of the avoidance of fouling.

Briefly, this object and other objects of the present invention as hereinafter will become more readily apparent can be attained by a process for the thermal after-treatment of cleavage product from the acid-catalyzed cleavage of cumene hydroperoxide into phenol and acetone which comprises heating the cleavage product in a reactor, wherein the heat supplied for the thermal treatment is the heat generated by at least one exothermic reaction which occurs in the reactor. The thermal treatment of the invention provides a high selectivity of the after-treatment combined with a lowering of the energy costs and a greater operating period of the heat exchangers because of the avoidance of fouling.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
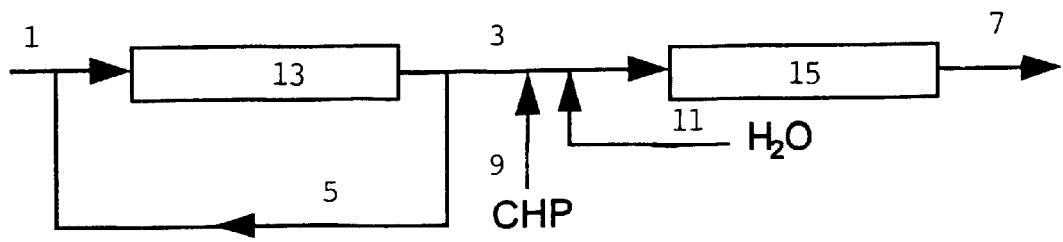
FIG. 1 shows an apparatus embodiment of a reactor for thermally cleaving CHP followed by a reactor for thermally after-treating the cleavage product.

In addition to the process of the invention, the invention likewise provides a reactor for preparing phenol and acetone by acid-catalyzed cleavage of cumene hydroperoxide, which has at least two regions of which at least one region is equipped with an apparatus for removing heat and at least one further region has plug flow characteristics.

The apparatus of the invention has the advantage that the actual CHP cleavage and the thermal after-treatment can be combined in one reactor.

The process of the invention has an advantage in that, compared to conventional processes, significantly less steam is required to heat the cleavage product to be subjected to thermal after-treatment. If the heat of reaction liberated in the thermal after-treatment of the cleavage product is sufficient, the use of steam for heating the cleavage product can be omitted entirely. In contrast to processes or other apparatuses in which steam or other suitable heat transfer media are continually used for heating the cleavage product, fouling occurs to a significantly lesser extent or not at all when using the process of the invention for treating the cleavage product.

The process of the invention is described below by way of example for the after-treatment of the cleavage product formed in the cleavage of CHP into phenol and acetone, without the process of the invention being restricted to this embodiment.

The process of the invention for the thermal after-treatment of cleavage product obtained in the acid-catalyzed cleavage of cumene hydroperoxide into phenol and acetone has the purpose of reducing the proportion of dimethyl phenyl carbinol (DMPC) and dicumyl peroxide (DCP) in the cleavage product, since these compounds react further with other compounds or with themselves to give high-boiling, tar-like compounds during the subsequent work-up of the cleavage product, in which a plurality of distillation steps for separation of materials are performed. These high-boiling compounds can interfere in the additional process steps which are performed for working-up the cleavage product. The formation of the high boilers also significantly reduces the yield in the overall process of the Hock phenol synthesis.

The thermal treatment or after-treatment of the invention of cleavage product cleaves the DMPC present into α-methylstyrene (AMS) and water and cleaves the DCP which is likewise present into phenol, AMS and acetone. The AMS formed in these reactions can be separated from the cleavage product during its further work-up and be hydrogenated to cumene which can be recirculated as starting material to the overall phenol production process. In this way, the yield losses caused by formation of by-products are reduced.

In order to conduct the abovementioned reactions, the cleavage product has to be heated to a certain temperature. It has been found that the conversion of DMPC into AMS and water is complete at temperatures above 110° C., even when DCP is not yet completely converted. For this reason, only the residual DCP content has to be checked after the thermal after-treatment in order to set optimum conditions for operation above 110° C. The residual DCP content in the cleavage product which has been after-treated thermally according to the invention is preferably from 0.01 to 0.05% by weight, preferably from 0.01 to 0.02% by weight. Higher values lead to a deterioration in the selectivity of the overall process above these DCP losses which can additionally lead to higher o-cresol contents in the pure phenol, while lower values of less than 0.01% by weight lead to excessively high by-product formation of high boilers from AMS during the thermal after-treatment. The residual DCP content is usually determined by analysis.

For the abovementioned reasons, the cleavage product to be after-treated thermally is heated to a temperature above 100° C., preferably above 115° C. This thermal after-treatment is also known as heat treatment.

For the after-treatment of the cleavage product, the product is transferred to a reactor, preferably a tube reactor, and heated. According to the invention, the heating of the cleavage product mixture is achieved by utilizing the heat of reaction evolved during at least one exothermic reaction in the cleavage product. One of such exothermic reactions is the acid-catalyzed cleavage of CHP. Since the heating of the cleavage product by utilization of the heat of reaction of an exothermic reaction occurs directly, indirect heat transfer by means of heat exchangers for heating the cleavage product may be able to be omitted entirely.

The cleavage of DMPC into AMS and water, and especially the cleavage of DCP into phenol, acetone and AMS also, both of which reactions are exothermic reactions, liberate heat of reaction which corresponds to a defined increase in the temperature of the cleavage product. This temperature difference is, depending on the initial DMPC and DCP contents, usually from 10 to 20° C. Typical DMPC concentrations are from 0.5 to 2% by weight. Typical DCP concentrations are in the range from 2 to 6% by weight. However, the process of the invention is not restricted to the concentrations indicated for DCP or DMPC.

The quantity of heat liberated in the abovementioned exothermic reactions has to be taken into account in the calculation of the initial concentration of CHP in the cleavage product prior to the thermal after-treatment necessary for heating the cleavage product to the desired temperature.

As a starting point for the calculation of the initial CHP concentration necessary, use can be made of the rule of thumb that the cleavage of a 1% strength by weight CHP solution liberates approximately the amount of heat necessary to increase the temperature of the solution from 6.8 to 7.0° C. Thus, a 6% strength by weight CHP solution would be heated from 40.8 to 42° C. by cleavage of all the CHP. The rule of thumb applies to the solutions usually used in the CHP cleavage. Such solutions usually comprise cumene, phenol and acetone, but only small amounts (from 0 to 15% by weight) of water. Because of the higher heat capacity of water, the cleavage of CHP in a solution or dispersion containing 99% by weight of water and 1% by weight of CHP would increase the temperature of this solution by only about 3.5° C. For this reason, the heating factor has to be determined afresh for cleavage mixtures which have a water content that is higher than usual. This determination can be conducted in a manner known to those skilled in the art using simple preliminary tests.

According to the invention, the additional CHP necessary for the generation of heat is added afterward to the cleavage product if sufficient CHP is not present in the cleavage product mixture.

Sulfuric acid is preferably used as catalyst for the cleavage of CHP. The cleavage product mixture preferably has a sulfuric acid concentration of from 50 to 1000 ppm. It can be advantageous to change the acid activity, i.e. the acid strength of the cleavage product, prior to the thermal treatment. The acid strength depends on the acid concentration and the concentration of water in the cleavage mixture. The higher the water content of the cleavage mixture, the more acid has to be added to the cleavage mixture in order to obtain the same acid activity, with the acid strength being proportional to the square of the water concentration. Thus, for example, the acid strength of a cleavage mixture solution containing 200 ppm of sulfuric acid and 2% by weight of water has only one sixteenth of the acid strength of a cleavage mixture solution containing 200 ppm of sulfuric acid and 0.5% by weight of water.

The ideal acid strength and thus the ideal composition of the cleavage mixture in respect of acid concentration and water concentration can be determined by simple preliminary tests. In the case of cleavage mixtures having a water concentration of up to 6% by weight, a sulfuric acid concentration of from 100 to 500 ppm in the cleavage mixture has been found to be particularly advantageous. In order to increase the acid strength, it is usual to add additional sulfuric acid. In order to reduce the acid strength, a base such as phenoxide solution, ammonia or aqueous sodium hydroxide, or water, can be added to the cleavage product. Preference is given to adding water to the cleavage product.

In a particularly preferred embodiment of the process of the invention, the cleavage product to be treated thermally has a CHP concentration which, in combination with the concentrations of other compounds which react exothermically during the cleavage reaction, liberates exactly that quantity of heat which results in the cleavage product mixture being heated to the temperature desired for the thermal after-treatment.

In this embodiment of the process of the invention, an amount of CHP resulting in a CHP concentration greater than the concentration necessary for the heating or the thermal after-treatment of the cleavage product mixture is added to a cleavage mixture prior to the cleavage. This cleavage mixture is cleaved in the usual fashion, with the cleavage mixture being kept in a temperature range ranging from 40 to 85° C., preferably from 45 to 75° C., by cooling. Only when the cleavage product has the desired CHP concentration and the cleavage product mixture can be heated to the desired temperature by the exothermic reaction or reactions is the cooling switched off in the case of batchwise operation or is the cleavage product mixture transferred to a reactor or reactor region for thermal after-treatment in which no cooling takes place in the case of continuous operation. The required residence times and thus the CHP concentrations can be determined by simple preliminary tests.

It can be advantageous to conduct the process of the invention in a reactor which is particularly suitable for this process, as described below. It can be particularly advantageous to conduct the cleavage of CHP and the thermal after-treatment of the cleavage product in one reactor. However, it is likewise possible to conduct the process of the invention in an apparatus as described in the prior art for performing cleavage and thermal after-treatment.

In a further particularly preferred embodiment of the process of the invention, additional CHP is added to the cleavage product having a CHP concentration insufficient to heat the cleavage product enough for the thermal after-treatment.

The CHP is preferably added as a concentrate containing from 65 to 90% by weight of CHP. The addition is preferably conducted in such a way that the CHP introduced is sufficiently well-mixed with the cleavage product. This can be ensured in a manner known to those skilled in the art, e.g. by means of internals which make complete mixing possible, e.g. static mixers. The CHP is preferably introduced on the suction side of the pump which pumps the cleavage product to be treated into the tube reactor. In this way too, complete mixing of the cleavage product with the CHP introduced is ensured. Sufficient mixing of the CHP with the cleavage product to be treated thermally is necessary in order to avoid local overheating of the cleavage product during the heat treatment.

The CHP concentration in the cleavage product necessary in the two embodiments of the process of the invention is, depending on the initial temperature of the cleavage product and on the initial DCP concentration, from 5 to 10% by weight. In order to calculate the CHP concentration necessary, the abovementioned rule of thumb can be employed. Thus, for example, at an initial temperature of the cleavage product of 40° C. and a DCP content of 4% by weight, the CHP concentration prior to entry into the thermal after-treatment necessary to bring the cleavage product to a final temperature of 115° C. is about 8.5%. The heating time to 100° C. is usually less than 30 seconds. In the subsequent actual heat treatment, the temperature of the mixer rises in the residence time reactor to a temperature of about 115° C. The residence time of the cleavage product mixture in the residence time reactor depends on the acid strength. Depending on the acid strength, the residence time is usually from 30 to 300 seconds.

After the thermal treatment of the cleavage product in the reactor, the treated cleavage product can be brought to a final temperature of usually from 40 to 70° C. in a cooler. The cleavage product which has been treated according to the invention is passed to further treatment or work-up. The thermally treated cleavage product is usually worked-up by separating acetone and phenol from one another and from other compounds present in the thermally treated cleavage product by distillation. The work-up of these cleavage product streams is known to those skilled in the art.

In all embodiments of the process of the invention, it may be advantageous to add water to the cleavage product prior to the thermal treatment. The amount of water added to the cleavage product prior to the thermal treatment is particularly preferably such that the concentration of water in the cleavage product ranges from 0.5 to 3.0% by weight, preferably from 1.5 to 2% by weight and very particularly preferably 1.8% by weight.

The cleavage product which has been treated thermally according to the invention has a DCP concentration ranging from 0.01 to 0.05% by weight, preferably from 0.01 to 0.02% by weight, and a DMPC concentration ranging from 0.05 to 0.2% by weight. CHP is no longer detectable in the thermally treated cleavage product.

The process of the invention can be used in all processes in which alkylaryl hydroperoxides are cleaved. Suitable alkylaryl hydroperoxides include, for example, cumene hydroperoxide, sec-butyl benzenehydroperoxide and also substituted alkylbenzene hydroperoxides or alkyl hydroperoxides of other aromatics, for example naphthalene. The process of the invention is preferably used in the after-treatment of cleavage product from the cleavage of alkylaryl hydroperoxides in which the cleavage is an exothermic reaction. However, it is also possible to use the process of the invention for after-treatment of cleavage product which is obtained by cleavage of more than one alkylaryl hydroperoxide. In this case, at least one of the cleavage reactions has to be an exothermic reaction. The process of the invention is very particularly preferably used for after-treatment of the cleavage product formed in the acid-catalyzed cleavage of CHP into phenol and acetone or for the cleavage of CHP with combined thermal after-treatment of the cleavage product.

The process of the invention can be conducted continuously or batchwise. The process of the invention is preferably conducted continuously.

The process of the invention can be used both for the after-treatment of cleavage product which is obtained as a heterogeneous phase in the cleavage and for the after-treatment of cleavage product which is obtained in a homogeneous phase in the cleavage.

It can be of advantage to conduct the process of the invention in a reactor which is particularly suitable for this process. Here, the acid-catalyzed cleavage of CHP and the thermal after-treatment of the cleavage product are conducted in one reactor. However, it is also possible to use the process of the invention in existing plants for the cleavage of CHP, which have at least one cleavage reactor and at least one other reactor for thermal after-treatment of the cleavage product, as shown, for example, in FIG. 1 and FIG. 2.

Preference is given to using a reactor in the present process for preparing phenol and acetone by acid-catalyzed cleavage of cumene hydroperoxide, which has at least two regions of which at least one region is equipped with an apparatus for removing heat and at least one other region has plug flow characteristics. In this type of reactor, the cleavage reactor and the reactor necessary for the thermal after-treatment are combined. This is achieved by using a reactor in which a temperature profile can be set. Such a reactor preferably has a temperature profile such that a temperature which is preferably used for the cleavage of CHP, for example a temperature of from 40 to 85° C., can be set in the region of the combined reactor in which the cleavage is to take place. This can be achieved, for example, by heat transfer facilities, e.g. heat exchangers, by means of which the mixture to be cleaved can be kept at the desired temperature, preferably by removal of heat of reaction, being present in at least one region of the reactor. One possible embodiment is, for example, the connection in series of a plurality of heat exchangers. The cleavage of CHP preferably takes place in this region. Furthermore, at least one region which preferably has plug flow characteristics and in which the thermal after-treatment is to take place is present in such a reactor of the invention. This region of the combined reactor preferably has no facilities for heating the cleavage product to be treated. It can be advantageous for this region of the reactor to have a facility for cooling the cleavage product mixture to be treated. However, if the process of the invention is operated sufficiently carefully, it is also possible to omit such cooling.

Depending on the embodiment of the process of the invention, it can be advantageous to provide the reactor of the invention for the cleavage of CHP and after-treatment of the cleavage product formed in the cleavage with at least one, preferably at least two, metering facilities which make it possible to introduce water and/or CHP, or a CHP-containing mixture, into the region of the reactor of the invention in which the thermal after-treatment of the cleavage product is to take place. A possible embodiment of such a reactor of the invention is shown by way of example in FIG. 3.

The region for thermal after-treatment in the combined reactor is preferably configured so that the parameters mentioned in the process of the invention, e.g. temperature, heating time and residence time, are maintained.

It can be to advantage for the combined reactor of the invention to be equipped with at least one facility for recirculating at least part of the cleaved cleavage product and/or at least part of the after-treated cleavage product to the reactor. The recirculation can be designed so that part of the cleavage product can be branched off prior to entry into the region of the reactor in which after-treatment takes place and can be recirculated to the feed to the reactor. However, it is also possible for the recirculation to be designed so that part of the thermally after-treated cleavage product mixture can be recirculated to the feed to the reactor or into the region of the reactor in which the thermal after-treatment of the cleavage product commences. It can likewise be advantageous to provide a combination of the recirculation procedures mentioned.

Figure 2:
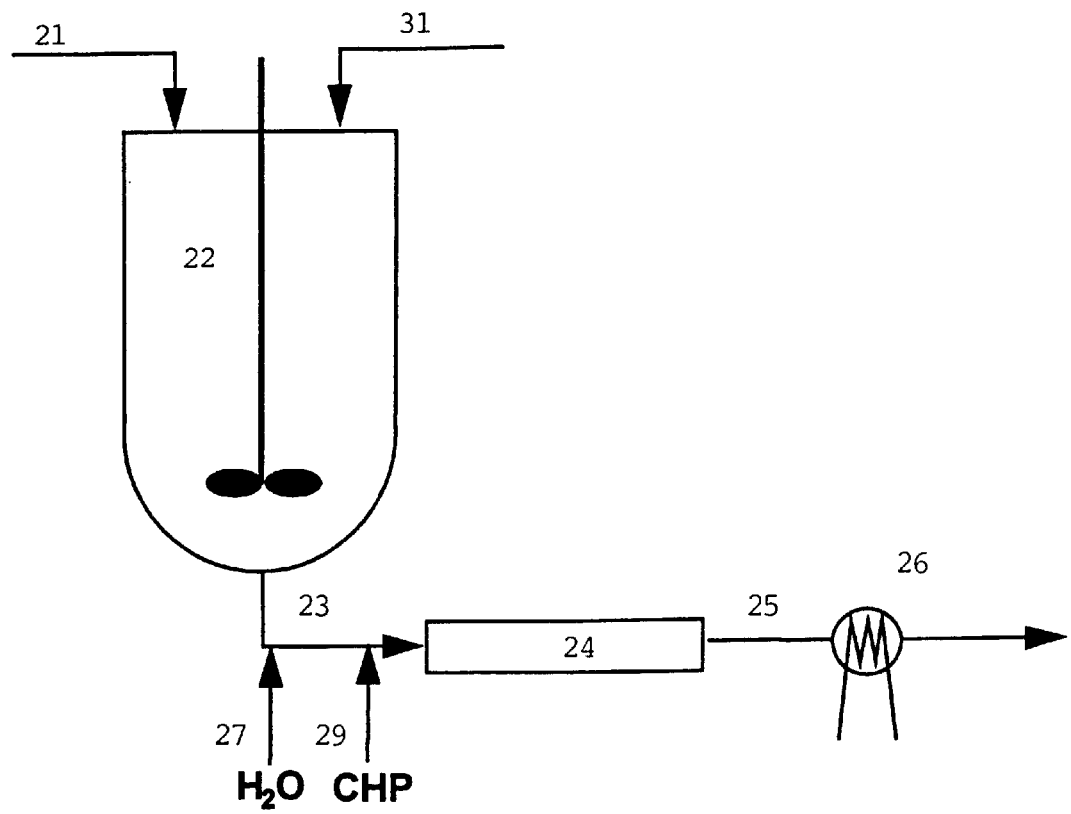
FIG. 2 shows another apparatus embodiment of a reactor for thermally cleaving CHP followed by a reactor for thermally after-treating the cleavage product.
Figure 3:
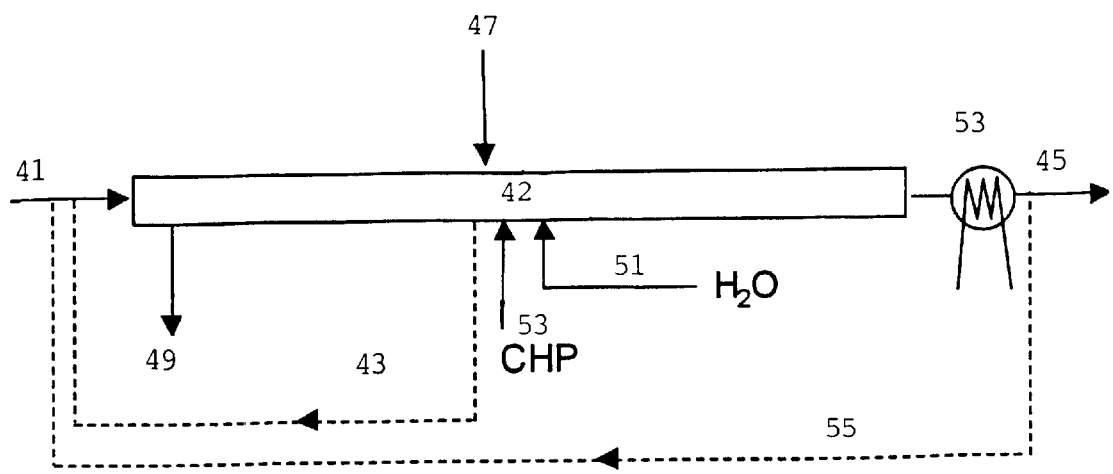
FIG. 3 shows a reactor embodiment provided with metering facilities which introduce water and/or CHP or a CHP containing mixture for thermal treatment.

Having now generally described this invention, a further understanding can be obtained by reference to certain specific examples, as well as by way of FIGS. 1–3, which are provided herein for purposes of illustration only and are not intended to be limiting unless otherwise specified.

FIG. 1 schematically shows a process for the cleavage of CHP. A mixture comprising the CHP to be cleaved is fed via line 1 into a first reactor, namely the cleavage reactor. The cleavage reactor 13 does not have to be only one reactor which may be configured, for example, as a tube reactor with recirculation or as a back-mixed apparatus; it is also possible for a plurality of reactors connected in series to be designated as the cleavage reactor. The cleavage product leaving the cleavage reactor 13 is, in the case of a tube reactor, at least partly recirculated via line 5 to the cleavage reactor. Via line 3, part of the cleavage product mixture is fed to a second reactor 15 in which the thermal after-treatment takes place. Upstream of the reactor 15, additional cumene hydroperoxide (CHP) and/or water ($H_2O$) can be introduced into the cleavage product mixture via two lines 9 and 11, respectively. The cleavage product mixture which has been subjected to thermal after-treatment leaves the reactor 15 via line 7 and can be passed to work-up.

FIG. 2 likewise shows a schematic diagram of the cleavage of CHP. A mixture comprising the CHP to be cleaved is fed via line 21 into a first cleavage reactor 22, which may be a back-mixed reactor. The catalyst necessary for the acid-catalyzed cleavage, e.g. sulfuric acid, can be metered into the cleavage reactor via line 31. The cleavage product leaving the cleavage reactor 22 is passed via line 23 to a second reactor 24 in which the thermal after-treatment takes place. Upstream of the reactor 24, additional cumene hydroperoxide (CHP) and/or water ($H_2O$) can be fed into the cleavage product mixture via two lines 29 and 27, respectively. The after-treated cleavage product mixture leaves the reactor 24 via line 25 and is discharged through a heat exchanger 26 by means of which the after-treated cleavage product mixture can be cooled is provided and the cleavage product mixture can be passed to work-up.

FIG. 3 schematically shows the cleavage of CHP in yet another reactor embodiment of the invention. A mixture comprising the CHP to be cleaved is fed via line 41 into a reactor 42, namely a combined cleavage and after-treatment reactor. This reactor 42 is preferably a tube reactor. Part of the reactor 42 can be maintained at a desired temperature by means of cooling, for which purpose coolant, e.g. water, is fed via 47 into, for example, a cooling jacket. The coolant leaves the reactor via line 49.

At the end of the section of the reactor provided with cooling or at the beginning of the section of the reactor not provided with cooling, a feed point 51 for water $H_2O$ and/or a feed point 53 for cumene hydroperoxide concentrate CHP can be provided. In the section of the reactor which has no cooling, thermal after-treatment of the cleavage product takes place by the cleavage product being brought to the desired temperature by means of the heat liberated in the cleavage of CHP. The thermally after-treated cleavage product mixture leaving the reactor can be cooled in a heat exchanger and passed via line 45 to work-up.

The reactor of the invention can be provided with one or more facilities for recirculating at least part of the after-treated cleavage product and/or at least part of the cleavage product. These facilities are shown as broken lines in FIG. 3. Thus, at least part of the cleavage product can be recirculated via line 43 into the reactor or by line 41 into the reactor. The after-treated cleavage product which has been cooled in the heat exchanger 53 can likewise be recirculated via line 55 into the reactor or by feed line 41 to the reactor.

EXAMPLES

Example 1

A cleavage product comprising 40% by weight of phenol, 4.0% by weight of DCP, 7.8% by weight of CHP and 0.8% by weight of DMPC and having an initial temperature of 50° C. and a sulfuric acid concentration of 200 ppm was heated to a temperature of 105° C. over a period of 30 seconds by cleavage of the CHP and the DCP. At a residence time of 120 seconds in the reactor, the cleavage of DCP and DMPC proceeded to completion at a temperature ranging from 105° C. to 120° C. The cleavage product mixture which had been after-treated in this way was cooled quickly back to a temperature of 45° C. in a heat exchanger. The residual DCP content of the thermally treated cleavage product was 0.02% by weight.

Example 2

A 67% strength CHP solution and water were metered into a cleavage product mixture comprising 40% by weight of phenol, 3.0% by weight of DCP, 0.8% by weight of DMPC and 2% by weight of CHP and having a temperature of 60° C. in such amounts that the cleavage product mixture contained 5.8% by weight of CHP and 1.8% by weight of water. The acid concentration was 500 ppm. The addition of CHP solution and water took place on the suction side of the pump which pumped the cleavage product to be treated through the reactor. As a result of the addition of the CHP, the exothermic cleavage of the CHP raised the temperature of the cleavage product mixture to a temperature of 100° C. At this temperature, DCP and DMPC cleavage commenced, with a temperature of up to 112° C. being established in the cleavage product mixture at a residence time of 230 seconds. The cleavage product mixture which had been after-treated in this way was cooled quickly back to a temperature of 45° C. in a heat exchanger. The residual DCP content of the thermally treated cleavage product was 0.01% by weight.

The disclosure of German priority Application Number 10021482.7 filed Mar. 5, 2000 is hereby incorporated by reference into the present application.

Obviously, numerous modifications and variations of the present invention are possible in light of the above teachings. It is, therefore, to be understood that within the scope of the appended claims, the invention may be practiced otherwise than as specifically described herein.

What is claimed as new and desired to be secured by Letters Patent of the United States is:

1. A process for the thermal after-treatment of cleavage product from the acid-catalyzed cleavage of cumene hydroperoxide to phenol and acetone, which comprises:
   subjecting cumene hydroperoxide to acid cleavage thereby producing a cleavage product containing phenol, acetone, unreacted cumene hydroperoxide and other minor products of the cleavage reaction, and
   conducting a thermal after-treatment on said cleavage product in a reactor at a temperature above 100° C., wherein the heat for the after-treatment is heat generated by at least the acid cleavage exothermic reaction of cumene hydroperoxide in the after-treatment reactor.

2. The process as claimed in claim 1, wherein the cleavage product to be treated has a cumene hydroperoxide concentration ranging from 5 to 10% by weight before the thermal after-treatment.

3. The process as claimed in claim 1, wherein cumene hydroperoxide is added to the cleavage product to be treated.

4. The process as claimed in claim 1, wherein water is added to the cleavage product to be treated.

5. The process as claimed in claim 1, wherein the cleavage product to be treated thermally is heated to a temperature above 115° C.

6. The process as claimed in claim 1, wherein the thermally treated cleavage product contains dicumyl peroxide in an amount ranging from 0.01 to 0.05% by weight.

7. The process as claimed in claim 6, wherein the thermally treated cleavage product contains dicumyl peroxide in an amount ranging from 0.01 to 0.02% by weight.

8. The process as claimed in claim 1, wherein the acid-catalyzed cleavage of cumene hydroperoxide and the thermal after-treatment of the cleavage product are conducted in one reactor.

9. A process of preparing phenol, comprising:
   subjecting cumene hydroperoxide to acid cleavage thereby producing a cleavage product containing phenol, acetone, unreacted cumene hydroperoxide and other minor products of the cleavage reaction, and
   conducting a thermal after-treatment on said cleavage product in a reactor at a temperature above 100° C., wherein the heat for the after-treatment is heat generated by at least the acid cleavage exothermic reaction of cumene hydroperoxide in the after-treatment reactor, thereby producing said phenol.

10. The process as claimed in claim 1, wherein the reactor is a tube reactor.

11. The process as claimed in claim 1, wherein said cleavage product has a sulfuric acid concentration of 50 to 1000 ppm.

12. The process as claimed in claim 9, wherein the acid-catalyzed cleavage of cumene hydroperoxide and the thermal after-treatment of the cleavage product are conducted in successive reactors.

* * * * *

UNITED STATES PATENT AND TRADEMARK OFFICE
CERTIFICATE OF CORRECTION

PATENT NO.    : 6,555,719 B2
DATED         : April 29, 2003
INVENTOR(S)   : Reinhard Sigg et al.

It is certified that error appears in the above-identified patent and that said Letters Patent is hereby corrected as shown below:

Column 9,
Line 45, "Mar. 5, 2000" should read -- May 3, 2000 --.

Signed and Sealed this

Eleventh Day of November, 2003

JAMES E. ROGAN
*Director of the United States Patent and Trademark Office*